United States Patent
Shibata

(10) Patent No.: US 11,938,230 B2
(45) Date of Patent: Mar. 26, 2024

(54) HEMOSTATIC MATERIAL AND WOUND DRESSING CONTAINING SAME

(71) Applicants: Artisan Lab Co., Ltd., Tokyo (JP); NIPRO Corporation, Osaka (JP)

(72) Inventor: Kazuhiko Shibata, Tokyo (JP)

(73) Assignees: Artisan Lab Co., Ltd., Tokyo (JP); NIPRO Corporation, Osaka (JP)

( * ) Notice: Subject to any disclaimer, the term of this patent is extended or adjusted under 35 U.S.C. 154(b) by 0 days.

(21) Appl. No.: 17/818,551

(22) Filed: Aug. 9, 2022

(65) Prior Publication Data

US 2022/0378974 A1 Dec. 1, 2022

Related U.S. Application Data

(63) Continuation of application No. 16/634,304, filed as application No. PCT/JP2017/027890 on Aug. 1, 2017, now abandoned.

(51) Int. Cl.
*A61L 15/28* (2006.01)
*A61L 15/44* (2006.01)
*C08B 15/06* (2006.01)

(52) U.S. Cl.
CPC .............. *A61L 15/28* (2013.01); *A61L 15/44* (2013.01); *C08B 15/06* (2013.01); *A61L 2300/418* (2013.01); *A61L 2400/04* (2013.01)

(58) Field of Classification Search
CPC .. A61L 2300/48; A61L 2400/04; A61L 15/28; A61L 15/44; C08L 1/00; C08B 15/06
USPC ......................................................... 514/57
See application file for complete search history.

(56) References Cited

U.S. PATENT DOCUMENTS

| | | | |
|---|---|---|---|
| 4,026,291 A | 5/1977 | Nagano et al. | |
| 4,921,691 A | 5/1990 | Stockel | |
| 5,558,861 A * | 9/1996 | Yamanaka | C08B 11/145 435/948 |
| 6,444,199 B1 | 9/2002 | Renn | |
| 2011/0052665 A1 | 3/2011 | Hardy et al. | |
| 2013/0184220 A1 | 7/2013 | Duft | |
| 2015/0283217 A1* | 10/2015 | Shi | A61K 47/38 424/94.67 |
| 2015/0306274 A1 | 10/2015 | Hardy et al. | |

FOREIGN PATENT DOCUMENTS

| | | |
|---|---|---|
| CN | 103724568 A | 4/2014 |
| CN | 104162184 A | 11/2014 |
| JP | 50150296 | 12/1975 |
| JP | 62183768 A | 8/1987 |
| JP | 63152601 A | 6/1988 |
| JP | 2002512087 A | 4/2002 |
| JP | 2011507860 A | 3/2011 |
| JP | 2011518592 A | 6/2011 |
| JP | 2013133287 A | 7/2013 |
| JP | 2015537004 A | 12/2015 |
| JP | 2017140231 A | 8/2017 |

OTHER PUBLICATIONS

Journal of the American college of Toxicoloy, 1988, 7(3), 335-351.*
Goy, R., et al., "A Review of the Antimicrobial Activity of Chitosan", Polimeros: Ciencia e Tecnologia, 19(3): 241-247 (2009).
Kannon, G.A., et al., "Moist Wound Healing with Occlusive Dressings", Dermatologic Surgery, 21(7): 583-590 (1995).
Poiz C-60H Product Specification, Kao Chemicals (retrieved on Oct. 4, 2017 from https://chemical.kao.com/jp/products/A0003001_jpja.html.
Suzuki, S., et al., "Randomized Trial Comparing New Chitosan-Based Bandage with Kaltostat Hemostatic Dressing to Control Bleeing from Hemodialysis Puncture Site", Nephrology Dialysis Transplantation, vol. 28, Supplement 1 (SP484), 2 pages, May 2013.
Tsai, T., et al., "Chitosan Augments Photodynamic Inactivation of Gram-Positive and Gram-Negative Bacteria", Antimicrobial Agents and Chemotherapy, May 2011, 55(5): 1883-1890.
International Search Report and Written Opinion for International Application No. PCT/JP2017/027890, "Hemostatic Material and Wound Dressing Material Containing Same", dated Oct. 17, 2017.
Baumann, H., et al., "Partially Cationized Cellulose for Non-Thrombogenic Membrane in the Presence of Heparin and Endothelial-Cell-Surface Heparansulfate", Journal of Membrane Science, vol. 61(1): 253-268. (Sep. 1991).
Luna-Straffon, Marco A., et al., "Wound debridement and antibiofilm properties of gamma-ray DMAEMA-grafted onto cotton gauzes", Cellulose, vol. 21(5): 3767-3779 (2014).
Supplemental European Search Report for EP Application No. 17920080, "Hemostatic Material and Wound Dressing Containing Same" dated Feb. 9, 2021.

(Continued)

*Primary Examiner* — Ganapathy Krishnan

(74) *Attorney, Agent, or Firm* — Hamilton, Brook, Smith & Reynolds, P.C.

(57) ABSTRACT

A hemostatic material is described, which eliminates the risks of conventional chitosan-derived products, such as the onset of shellfish allergy and endotoxin contamination, can be used safely for more people, and has an antibacterial property and a hemostatic function that widely-used hydrogels lack, and a wound dressing containing the same. A hemostatic material containing cationized cellulose and a wound dressing containing the hemostatic are described. At least one of hydroxyl groups of the cationized cellulose is modified with $-R^2-N^+(R^3)(R^4)(R^5) \cdot X^-$, other hydroxyl groups of the cationized cellulose have $-H$, or $-(CH_2CH_2O)_m-H$, $R^2$ represents $C_{1-6}$ alkylene, $C_{2-6}$ hydroxyalkylene, $-(CH_2CH_2O)_{l}-$, or a combination thereof, l represents 1 or 2, m represents 1 or 2, and $X^-$ may represent an anionic group.

9 Claims, 1 Drawing Sheet

(56) References Cited

OTHER PUBLICATIONS

Non-Final Office Action for U.S. Appl. No. 16/634,304 "Hemostatic Material And Wound Dressing Containing Same" dated Jun. 16, 2022.
Final Office Action for U.S. Appl. No. 16/634,304 "Hemostatic Material And Wound Dressing Containing Same" dated Dec. 29, 2021.
Final Report on the Safety Assessment of Polyquaternium-10, Journal of the American College of Toxicology, 7(3): 1988, 335-351.

* cited by examiner

HEMOSTATIC MATERIAL AND WOUND DRESSING CONTAINING SAME

RELATED APPLICATIONS

This application is a continuation of U.S. application Ser. No. 16/634,304, filed Jan. 27, 2020, which is the U.S. National Stage of International Application No. PCT/JP2017/027890, filed Aug. 1, 2017, which designates the U.S. and published in Japanese. The entire teachings of the above applications are incorporated herein by reference.

TECHNICAL FIELD

The present invention relates to a hemostatic material, and a wound dressing containing the hemostatic material.

BACKGROUND ART

Known skin wound healing mechanisms are such that (1) when the skin is damaged, platelets gather around and in the wound and coagulate the blood to stop bleeding, (2) neutrophils and macrophages gather around the wound to phagocytose and remove necrotic tissue and bacteria, (3) fibroblasts gather to shrink the wound, and (4) epidermal cells migrate and gather to epithelialize the wound.

For wound healing, various living cells are required to gather and function around and in the wound as described above. Many cytokines including growth factors summon cells required for wound healing to the wound. It is important for quick wound healing to maintain an environment where cells gathered around and in the wound by cytokines can actively function.

In the past, the mainstream idea was that a wound should be dried to heal the wound. However, when the wound is dried, biological cells die and re-epithelialization is less likely to occur. In order to solve this problem, moist wound healing has rapidly spread in recent years, and has been widely applied clinically as one of wound repair techniques. The moist wound healing is known to keep a wound site moist with an exudate generated from the site so as to prevent the wound from drying, allowing active cell division to take place at the wound and resulting in quick wound healing (NPTL 1). A wound dressing is a member that provides a moist environment by covering a wounded site and promotes wound healing.

Hydrogels, which are widely used as components of wound dressings, have no effect in regard to as antibacterial and hemostatic properties and, it is not easy to degrade some kinds of hydrogels by microorganisms when buried in the soil. For this reason, some kinds of hydrogels are disposed by incineration or burying, and may generate dioxin if the temperature of a combustion furnace falls upon incineration. In the case of disposal by burying, securing of a burial place is becoming difficult, and thus a product causing no dioxin generation by incineration and having a small environmental burden is required.

Further, many tests and examinations are carried out at actual medical sites for wound repair materials such as sutures and artificial bones made from chitosan as a raw material. As a result, hemostatic materials and wound dressings produced using chitosan as a raw material are under development (PTLs 1 and 2). Chitosan has an amino group, and is positively charged depending on conditions to aggregate blood cells and to exhibit a hemostatic effect. Chitosan has been considered to be an ideal component of a hemostatic material and a wound dressing, because chitosan also produces an antibacterial effect (NPLs 2 and 3).

CITATION LIST

Patent Literature

[PTL 1] Japanese Translation of PCT International Application, Publication No. 2011-518592
[PTL 2] Japanese Unexamined Patent Application, Publication No. 2013-133287

Non Patent Literature

[NPL 1] GEORGIA A. KANNON, ALGIN B. GARRETT, Moist Wound Healing with Occlusive Dressings, Dermatologic Surgery, Volume 21, Issue 7, p. 583-590, July, 1995
[NPL 2] Rejane C. Goy, Douglas de Britto, Odilio B. G. Assis, A review of the antibacterial activity of chitosan, Polimeros, vol. 19, no. 3, p. 241-247, 2009
[NPL 3] Tsuimin Tsai, Hsiung-FeiChien, Chitosan Augments Photodynamic Inactivation of Gram-Positive and Gram-Negative Bacteria, Antimicrobial Agents Chemotherapy, 2011 May, 55(5), p. 1883-1890

SUMMARY OF INVENTION

Technical Problem

However, chitosan could be an allergen leading to shellfish allergy, and the use of a hemostatic material or a wound dressing made of chitosan as a raw material may cause a severe allergic reaction in a person who is allergic to shellfish. When a formulation produced with chitosan as a raw material is used for wounds, and specifically, when such a formulation is prescribed for a person with a shellfish allergy, care should be taken and another formulation should be used if possible. However, there is a potential risk of developing allergy since a person being prescribed may not be previously noticed that he/she has a shellfish allergy. Further, crab or shrimp crusts, which are not originally sterile, are used as a raw material for mass production of chitosan. Hence, it is difficult to completely remove endotoxins, which are secreted by bacteria and harmful to human bodies, when chitosan is isolated. Known pathological conditions induced by endotoxins include lethal shock, fever, activation of complements, activation of leukocytes, and damage to vascular endothelial cells, etc.

On the other hand, components of wound dressings widely used other than chitosan, such as hydrogels, lack antibacterial and hemostatic properties, etc. Accordingly, bacterial growth within a wound covered with a wound dressing can interfere with wound healing and cause serious complications.

The present invention has been achieved in view of such circumstances, and an object of the present invention is to provide a hemostatic material and a wound dressing containing the hemostatic material, which can be used safely for more people, and also suppresses bleeding and infection which hinder wound healing, and hardly causes complication.

Solution to Problem

In order to solve the above problems, a first aspect of the present invention provides a hemostatic material comprising cationized cellulose. Another aspect of the present invention provides a wound dressing comprising a hemostatic material containing cationized cellulose as a component. Yet another aspect of the present invention provides a wound dressing comprising cationized cellulose.

Cellulose is a natural compound produced by plants in their bodies through photosynthesis. In recent years, since cellulose can provide a suitable wound healing environment by absorbing and releasing water, wound dressings mainly made of cellulose, such as Dermafill and XCell Cellulose Wound Dressings, are commercially available. In addition, wound dressings containing carboxymethyl cellulose, which is a cellulose derivative, have been put to practical use. Unlike chitosan which causes shellfish allergy, cellulose contained in plants and the like, which are ingested daily, is used, and cellulose is safer than chitosan in view of possible allergic onset. However, these products have water-holding capacity, but lack antibacterial and hemostatic properties. Therefore, wound dressings containing cellulose or carboxymethyl cellulose as a main component cannot suppress internal bacterial growth and bleeding complications when wounds are covered.

In contrast, unlike cellulose and carboxymethyl cellulose, cationized cellulose has a positively charged functional group and thus has both hemostatic and antibacterial properties. The hemostatic property was examined and confirmed using activated clotting time. With regard to the antibacterial property, it was confirmed that cationized cellulose has an antibacterial property through culturing of skin indigenous bacteria of medical practitioners in an agar medium, followed by formation of a blocking circle around the filter paper impregnated with the gelled cationized cellulose during bacterial culture.

In the present invention, cationized cellulose is contained in a hemostatic material or a wound dressing that directly contacts a wound. In this manner, the hemostatic material or the wound dressing directly contacts bacteria at the wound site, whereby the cationized cellulose can exhibit antibacterial activity due to the positive charge of the cationized cellulose.

In the present invention, the above cationized cellulose may be of formula (1):

Chemical formula 1

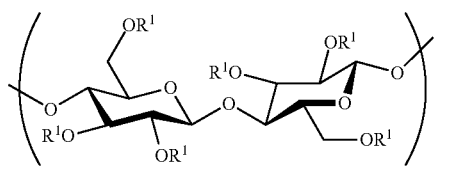

(1)

wherein
at least one of $R^1$ represents —$R^2$—$N^+(R^3)(R^4)(R^5).X^-$,
other $R^1$ each represent —H, or —$(CH_2CH_2O)_m$—H,
$R^2$ represents $C_{1-6}$ alkylene, $C_{2-6}$ hydroxyalkylene, —$(CH_2CH_2O)_l$—, or a combination thereof,
l represents 1 or 2,
m represents 1 or 2,
$X^-$ represents an anionic group, and
$R^3$, $R^4$ and $R^5$ each represent $C_{1-6}$ alkyl, $C_{1-6}$ alkenyl, O—$C_{1-6}$ alkyl, $C_aY_b$ heteroalkyl or heteroalkenyl, wherein Y represents a hetero atom, (a+b) ranges from 4 to 6, and a saturated or unsaturated 5- or 6-membered ring containing a nitrogen atom is formed upon binding with the nitrogen atom.

In the present invention, the at least one $R^1$ represents —$CH_2CH_2O$—$CH_2CH(OH)CH_2$—$N^+(R^3)(R^4)(R^5).X^-$, and $R^3$, $R^4$ and $R^5$ may represent a methyl or an ethyl group. In the present invention, the at least one $R^1$ may represent —$CH_2CH(OH)CH_2N^+(R^3)(R^4)(R^5).X^-$, and $R^3$, $R^4$ and $R^5$ may each represent a methyl or an ethyl group. In the present invention, the anionic group may be a halide ion, a phosphoric acid ester group, a carboxyl group, a sulfonic acid group, a sulfuric acid ester group or the like. The halide ion may be a fluoride ion, a chloride ion, a bromide ion, or an iodide ion.

With the above configuration, cationized cellulose can be obtained more easily.

In the above configuration, at least one of the other $R^1$ may also represent —$(CH_2CH_2O)_m$H.

With the above configuration, the water-holding capacity of cationized cellulose can be increased. This broadens the range of applicable conditions and makes it possible to produce a wound dressing more suitable for moist treatment.

Advantageous Effects of Invention

The hemostatic material and the wound dressing according to the present invention can be used safely for more people, and, can promote wound healing. Further, compared to commonly used hydrogels, the hemostatic material and the wound dressing function to suppress bleeding, infection and the like, and thus have high safety and can lower risks such as cellulitis and septicemia. Furthermore, unlike chitosan, a hemostatic and a wound dressing, which are free of shellfish allergy concerns, can be provided.

DESCRIPTION OF EMBODIMENTS

Figure 1A:
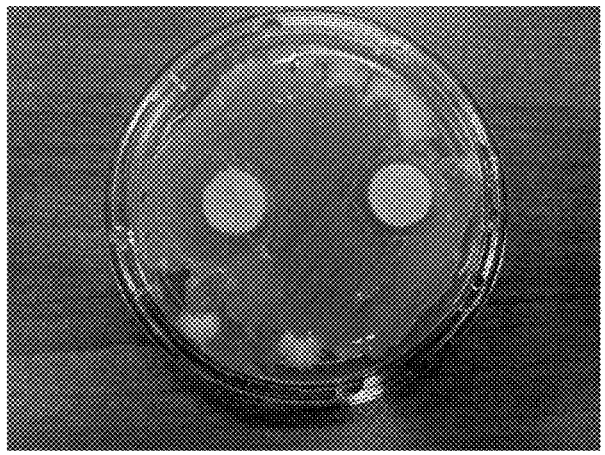
FIG. 1A is the image of a medium demonstrating the antibacterial property of cationized cellulose in one embodiment of the present invention.

Hereinafter, one embodiment of the hemostatic material and the wound dressing according to the present invention will be described. The general formula representing cationized cellulose contained in the hemostatic material and the wound dressing according to the present embodiment is shown below. Any of the 2-, 4- and 6-position hydroxyl groups of glucose that forms cellulose is modified with a cationized functional group.

Chemical formula 2

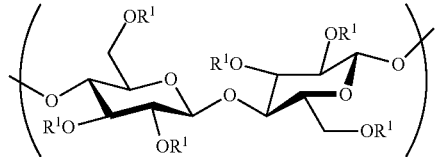

The cationized cellulose used in the present embodiment can be purchased as a commercial product, and can be synthesized by applying a general synthesis method employed for chemical modification of glucan.

SYNTHESIS EXAMPLE 1

Synthesis of 2-hydroxy-3-trimethylammoniopropylcellulose chloride 3-chloro-2-hydroxypropyltrimethylammonium chloride (2.3 g) as a cationizing agent is added to a solution prepared by dissolving 1.0 g of cellulose in 20 mL of a 1N sodium hydroxide aqueous solution, and then the solution is stirred at 30° C. to 50° C. The resulting solution is neutralized with 4N acetic acid and then separated by dialysis membrane using distilled water. The obtained solution is lyophilized, so that a desired product can be obtained.

SYNTHESIS EXAMPLE 2

Synthesis of 6-hydroxyethyl-(2-hydroxy-3-trimethylammoniopropyl)cellulose chloride Cellulose (2.0 g) is reacted with ethylene oxide under known conditions to synthesize hydroxyethyl cellulose. Glycidyl trimethyl ammonium chloride (4.5 g) as a cationizing agent is added to a solution prepared by dissolving the obtained hydroxyethyl cellulose in 20 mL of a 1N sodium hydroxide aqueous solution, and then the solution is stirred at 30° C. to 50° C. The resulting solution is neutralized with 4N acetic acid and then separated by dialysis membrane using distilled water. The obtained solution is lyophilized, so that a desired product can be obtained.

A cationized cellulose having different types of substituents can be synthesized in the same manner as the above synthesis example. As a solvent to be used herein, an alcohol such as methanol or ethanol, acetonitrile or the like may be added depending on the solubility of the substrate. The equivalent of the cationizing agent to be reacted can be appropriately adjusted according to the degree of cationization of target cationized cellulose.

Experiment for Confirmation of Antibacterial Activity of Cationized Cellulose

The degree of bacterial sensitivity to the cationized cellulose according to the present invention was confirmed by a disc method. ASONE SANYFOODS Petan Check 25 PT4025 standard agar medium was used to culture bacteria attached to the bare hands of 3 medical personnels. Bacteria actively forming colonies of these bacteria were collected with sterile cotton swabs and applied in equal amounts to three media (Medium 1, Medium 2, Medium 3). As cationized cellulose, 1 g of hydroxyethyl cellulose hydroxypropyl trimethyl ammonium chloride ether (Kao POIZ C-60H, C-150 L) was used, and 4 mL of water for injection was added thereto and then the mixture was stirred for 3 minutes. Filter paper was impregnated with the resulting gelled sample and then placed on the above media. After culturing at 37° C. for 48 hours, the formation of inhibition circles was confirmed.

Figure 1B:
FIG. 1B is the image of another medium demonstrating the antibacterial property of cationized cellulose in one embodiment of the present invention.
Figure 1C:
FIG. 1C is the image of yet another medium demonstrating the antibacterial property of cationized cellulose in one embodiment of the present invention.

The results of the experiment for confirmation of the antibacterial activity are shown in FIGS. 1A to 1C. In all of Medium 1 (FIG. 1A), Medium 2 (FIG. 1B) and Medium 3 (FIG. 1C), inhibition circles were observed around the discs impregnated with the cationized cellulose gel. In each figure, the result of using the filter paper impregnated with POIZ C-60H is shown on the left and the result of using the same impregnated with POIZ C-150L is shown on the right, and both groups of POIZ C-60H and POIZ C-150L exhibit equivalent antibacterial property. The bacteria grew in the media were, as a result of identification, a mixture of *staphylococci* and bacteria of the genus *Bacillus* in Medium 1, bacteria of the genus *Bacillus* in Medium 2, and *staphylococci* in Medium 3. This successfully confirmed that the cationized cellulose has antibacterial activity.

Experiment for Confirmation of Hemostatic Property of Cationized Cellulose

The hemostatic property of the cationized cellulose according to the present invention was confirmed by comparing the clotting time with that of a control substance using a dedicated cartridge for blood coagulation measurement device (JMS Co., Ltd.). The average weight was determined by measuring 10 pieces of diatomaceous earth originally enclosed in dedicated cartridges for a blood coagulation measurement device specialized for an elapsed-time timer, "ACTester" (QUEST Medical, Inc.) for measuring clotting time. The average weight of the diatomaceous earth pieces in the lot used herein was 0.015 g, and thus cartridges were each prepared by replacement with cationized cellulose (Kao POIZ C-60H, C-150 L) having the same weight as that of the diatomaceous earth piece. Whole blood (0.7 mL) was collected from a subject (the inventor in this case) using a needle for injection with the outer diameter of 0.7 to 1.2 mm (22 to 18 G) of a needle tube and a 1 cc syringe. Immediately after blood collection, 0.7 mL or less of blood was injected into a dedicated cartridge for blood coagulation measurement device. Before removing the needle from the cartridge, 0.7 mL of air in the cartridge was withdrawn. After blood and the blood coagulation promoter were thoroughly mixed, the cartridge was set in the ACTest tube holder of the device body to measure the activated clotting time.

Measurement results are shown in Table 1. Student's t-test was used for the significant difference test.

TABLE 1

| | Activated clotting time (second) | | | | | Average (second) value | Standard Deviation | t-test for diatomaceous earth |
|---|---|---|---|---|---|---|---|---|
| | Test 1 | Test 2 | Test 3 | Test 4 | Test 5 | | | |
| Diatomaceous earth | 102 | 103 | 99 | 105 | 98 | 101.4 | 2.9 | — |
| C-60H | 76 | 31 | 70 | 45 | 75 | 59.4 | 20.3 | 0.00691 |
| C-150L | 56 | 44 | 58 | 59 | 68 | 57.0 | 8.6 | 0.00034 |
| Chitosan | 328 | 265 | 320 | 369 | 177 | 291.8 | 74.1 | 0.00207 |

The above results could confirm that the cationized cellulose has effects of promoting coagulation and stopping bleeding. Further, the results could also confirm that the cationized cellulose has hemostatic property higher than that of chitosan which is generally used for wound dressings.

The inventors of the present invention have discovered that through chemical modification of cellulose with a cationized functional group, a hemostatic material and a new wound dressing having an antibacterial function and a hemostatic function can be provided. Advantages brought by such hemostatic and antibacterial functions to wound healing are discussed below.

Hemostatic Function

It is not an argument that we have to stop bleeding at the wound site immediately after injury. At present, as a wound dressing to be used when bleeding occurs at a wound site, KALTOSTAT (registered trademark) containing alginate, a dressing containing chitosan, etc., are considered as the first choice. However, alginic acid has a weak hemostatic function compared to chitosan (Syota Suzuki, Kazuhiko Shibata, Randomized Trial comparing New Chitosan-Based Bandage with Kaltostat Hemostatic Dressing to Control Bleeding from Hemodialysis Puncture Site, Nephrol. Dial. Transplant., 2013, 28 (Suppl 1), i226-i239.) and chitosan has low water-holding ability, so neither is sufficient as bases for moist treatment. A dressing containing chitosan used herein, which is provided by HemCon Medical Technologies Inc., in the United States, is known to rapidly close a bleeding area and stop bleeding when applied to the bleeding area, as the chitosan attracts red blood cells and platelets in the blood. Such a function is considered to be due to the fact that chitosan is positively charged depending on conditions. Therefore, through the use of cationized cellulose that is always positively charged regardless of the pH of the surrounding environment as a component of a dressing to be used at an early stage of injury, a dressing having a hemostatic function higher than that of chitosan can be provided.

There remains also a risk of bleeding even after transition to moist treatment. When wounds are covered with a hydrogel, such as DuoACTIVE (registered trademark) that has been used in the past, bleeding may not be noticed if bleeding occurs during sleep or unconsciousness, which can result in hemorrhaging. Further, when hematoma is formed in a closed, moist environment, there is no immunological antibacterial activity in the hematoma, and thus *Staphylococcus aureus* etc., increase explosively in the warm, moist and nutrient-rich hematoma. One *Staphylococcus* may divide every 26 minutes and can increase to 2 million *S. aureus* after only 10 hours. Bacterial groups typified by this enormous amount of *S. aureus* injure human cell groups that are gathering for wound healing, adversely affecting wound healing. For this reason, eliminating foreign substances such as hematomas on the wound surface is an important factor for early treatment. Furthermore, the hemostatic function is also an effective additional function in wound healing, in order to inhibit the formation of foreign substances or hematomas serving as culture media for bacteria after bleeding.

Antibacterial Function

Bacterial groups with short cell division times overwhelm living cells in terms of growth rates and delay wound healing. In recent years, a method that has been widely spread involves frequently replacing dressings attached to a wound site and cleaning the wound site every replacement. This is because a problem is becoming clear such that sealing the wound site by leaving a dressing applied to the wound site results in the formation of an environment suitable for the growth of bacteria present at the wound site, which in turn delays the healing of the wound site.

The hemostatic material and the wound dressing according to the present invention can solve the problems as described above by containing positively charged cationized cellulose. The bacterial cell surface at around neutrality is negatively charged by dissociation of phosphate and carboxyl groups. Positively charged cationized cellulose, which is present in the vicinity of the surface where a hemostatic contacts the wound, or the surface of the wound dressing, electrostatically adsorbs to the bacterial cell surface, so that bacteria can be efficiently captured. Furthermore, bacteria captured in the vicinity of the surface where a hemostatic comes into contact with the wound and the surface of the wound dressing are incorporated into the hemostatic material and the wound dressing, so that the bacteria can be removed from the wound site and wound healing can be accelerated.

Therefore, when bleeding is accompanied at an early stage of injury, the hemostatic material and the wound dressing can be used to stop bleeding. When the wound site is washed after hemostasis and occlusive dressing is performed, the use of the wound dressing containing cationized cellulose having an antibacterial effect according to the present embodiment can reduce the adverse effects of bacteria more effectively than the conventional method that involves continuously applying a wound healing drug lacking such antibacterial effect. Further, the use of a chitosan preparation requires a caution when it is applied to a person with a shellfish allergy. In contrast, the cationized cellulose is less likely to be of concern and can be safely used by more people.

Further, cationized cellulose has a high water-holding capacity, and thus is gelled by incorporating excess water at the wound site. This makes it possible to maintain an ideal environment for leaving the exudate containing various substances important for wound healing on the surface of the wound for a long time while suppressing bacterial growth at the wound site.

Next, the aspects of hemostatic materials and wound dressings containing cationized cellulose are described.

As a hemostatic material in the present embodiment, cationized cellulose can be gelled. Accordingly, a hemostatic material containing cationized cellulose can be applied directly to the wound site. Even if the wound is irregular in shape, the hemostatic is applied in this manner, so as to be able to ensure its contact with the wound surface. Moreover, the applied gel is covered and pressed with a gauze, a film or the like, so that hemostasis can be achieved. After confirmation of hemostasis, it is also possible to release the pressure and use continuously the gel as a wound dressing.

As a wound dressing in this embodiment, cationized cellulose can be made into a sheet-like film. Specifically, once cationized cellulose is dissolved in a solvent such as water or alcohol to be gelled, the solvent can be forcibly discharged from the gel to form a film. The film can be adjusted in thickness, density and the like according to the purpose of use.

For the contact surface where the wound dressing contacts the wound, cationized cellulose as a simple substance or a mixture of cationized cellulose and a base may be formed into a film. If a water-soluble adhesive is used for adhering the wound dressing to the skin, the cationized cellulose in the film does not contact dry skin, while on the wound surface the water-soluble adhesive is dissolved because of an exudate from the wound. Hence, the cationized cellulose can be caused to contact only the wound surface. The opposite side of the contact surface can be reinforced or provided with additional performance through the use of a film that impedes the transpiration of water, or a cloth, non-woven fabric or the like that causes the water to transpirate appropriately when there is a large amount of an exudate. In this manner, preparations are used properly such that a preparation with a waterproof film is used in a dry state and a preparation with a water-permeable sheet is used when exfoliation likely takes place due to a large amount of an exudate and waterproofing. Hence, coatings suitable for various wounds can be prepared.

Further, as the wound dressing in the present embodiment, the obtained cationized cellulose can be gelled and contained in the wound dressing. Cationized cellulose has a water-holding capacity higher than that of chitosan. Therefore, the cationized cellulose is formed into a sheet or gel, the sheet or gel is applied to the wound site, and then a pad having water absorbability is applied thereon, so that even when a large amount of an exudate is generated from the wound site, the pad absorbs excess water and thus the moist environment at the wound site can be properly maintained as an environment required for healing.

Moreover, as described above, cationized cellulose has an antibacterial property. Therefore, even in a situation where cationized cellulose in the form of film or gel contacts directly the wound site, an antibacterial environment more suitable for healing can be maintained until wound healing. A waterproof film may be replaced by a breathable film in case the amount of an exudate is further increased.

The wound dressing according to the present embodiment is made into forms as described above, so that a user can conveniently apply the wound dressing to a wound site. Moreover, cationized cellulose can also be used as a hemostatic gauze by mixing cationized cellulose with or adsorbing cationized cellulose to cloth or non-woven fabric.

The wound dressing in the present embodiment may be a wound dressing such that after cationized cellulose is gelled and then the gel is applied to a wound site, the portion coated therewith can be covered with a water-permeable or waterproof sheet as necessary. With such a form, the wound dressing can be easily applied to the wound site even if the wound site has a complicated shape such as a cut and a deep crease.

There are cases in which wounds are accompanied by a large amount of an exudate or hemostasis is difficult. In order to cope with such wounds, the wound dressing in the present embodiment can be made into powder by adding a suitable base to cationized cellulose, or by performing processing such as spray drying or lyophilization. If there is a large amount of bleeding or an exudate from the wound site, the powder is sprinkled over the wound site to cover the site, and then the site is covered with gauze, a waterproof film, a water-absorbable sheet or the like. With such a form, the wound dressing can be easily used as a hemostatic at an early stage of injury, and the wound dressing according to the present embodiment can be applied with high freedom to cover wound sites in various shapes.

According to this embodiment, cellulose is chemically modified with a cationized functional group to positively charge the cellulose, thereby suppressing bacterial growth that hinders wound healing. Therefore, a hemostatic material and a wound dressing having antibacterial property better than that of conventionally used materials can be provided.

According to the present embodiment, positively charged cationized cellulose is used, so that a wound dressing having a higher hemostatic effect can be provided.

The invention claimed is:

1. A method for stopping bleeding at a bleeding wound site, comprising applying cationized cellulose having water-holding property and hemostatic properties of absorbing and coagulating blood to the bleeding wound site to stop the bleeding at the wound site wherein the cationized cellulose is of formula (1):

wherein

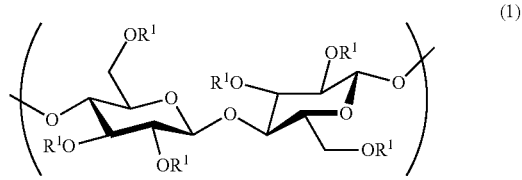

(a) at least one $R^1$ in the formula (1) represents $-CH_2CH_2O-CH_2CH(OH)CH_2-N^+(R^3)(R^4)(R^5).X^-$, and $R^3$, $R^4$ and $R^5$ are independently a methyl group or an ethyl group, or (b) at least one $R^1$ in the formula (1) represents $-CH_2CH(OH)CH_2N^+(R^3)(R^4)(R^5).X^{31}$, and $R^3$, $R^4$ and $R^5$ are independently a methyl group or an ethyl group wherein $X^-$ represents an anionic group, other $R^1$ each represent $-H$, or $-(CH_2CH_2O)_m-H$; where m is 1 or 2.

2. The method according to claim 1, wherein at least one of the other $R^1$ represents $-(CH_2CH_2O)_mH$.

3. The method according to claim 1, wherein the cationized cellulose is in the form of a gel, sheet-like film or a powder.

4. The method according to claim 1, wherein the anionic group is a halide ion, a phosphoric acid ester group, a carboxyl group, a sulfonic acid group or a sulfuric acid ester group.

5. The method according to claim 3, wherein the powder is a spray-dried powder or a lyophilized powder.

6. The method according to claim 1, wherein the cationized cellulose has a water-holding capacity that is higher than chitosan.

7. The method according to claim 1, wherein the cationized cellulose has a hemostatic property that is higher than chitosan.

8. The method according to claim 1, wherein the cationized cellulose further has an antibiotic property.

9. The method according to claim 1, wherein the cationized cellulose is applied to the wound site as a hemostatic gauze having the cationized cellulose mixed in or absorbed to cloth or a non-woven fabric.

* * * * *

UNITED STATES PATENT AND TRADEMARK OFFICE
CERTIFICATE OF CORRECTION

| | | |
|---|---|---|
| PATENT NO. | : 11,938,230 B2 | Page 1 of 1 |
| APPLICATION NO. | : 17/818551 | |
| DATED | : March 26, 2024 | |
| INVENTOR(S) | : Kazuhiko Shibata | |

It is certified that error appears in the above-identified patent and that said Letters Patent is hereby corrected as shown below:

In the Claims

In Claim 1, Column 10, Line 14, delete "wherein".

In Claim 1, Column 10, immediately following the formula on Line 25, insert -- wherein --.

In Claim 1, Column 10, Line 27, delete "–$CH_2CH_2O$–$CH_2CH(OH)CH_2$–$N^+(R^3)(R^4)(R^5)$.$X^-$," and insert -- –$CH_2CH_2O$–$CH_2CH(OH)CH_2$–$N^+(R^3)(R^4)(R^5)$·$X^-$, --.

In Claim 1, Column 10, Lines 31-32, delete "–$CH_2CH(OH)CH_2N^+(R^3)(R^4)(R^5)$.$X^{31}$," and insert -- –$CH_2CH(OH)CH_2N^+(R^3)(R^4)(R^5)$·$X^-$, --.

In Claim 1, Column 10, Line 34, delete "$X^-$represents" and insert -- $X^-$ represents --.

Signed and Sealed this
Thirtieth Day of April, 2024

Katherine Kelly Vidal
*Director of the United States Patent and Trademark Office*